United States Patent
Yin et al.

(10) Patent No.: US 11,738,083 B1
(45) Date of Patent: Aug. 29, 2023

(54) BODIPY-BASED RHOMBIC METAL RING, PREPARATION METHOD THEREOF, AND APPLICATION IN NEAR-INFRARED REGION IMAGING

(71) Applicant: Hangzhou Normal University, Hangzhou (CN)

(72) Inventors: Shouchun Yin, Hangzhou (CN); Yang Li, Hangzhou (CN); Huayu Qiu, Hangzhou (CN)

(73) Assignee: Hangzhou Normal University, Hangzhou (CN)

( * ) Notice: Subject to any disclaimer, the term of this patent is extended or adjusted under 35 U.S.C. 154(b) by 0 days.

(21) Appl. No.: 18/182,287

(22) Filed: Mar. 10, 2023

Related U.S. Application Data

(63) Continuation of application No. PCT/CN2022/100790, filed on Jun. 23, 2022.

(30) Foreign Application Priority Data

Apr. 20, 2022 (CN) .......................... 202210419349.3

(51) Int. Cl.
| | |
|---|---|
| *C07F 15/00* | (2006.01) |
| *C07F 5/02* | (2006.01) |
| *A61K 41/00* | (2020.01) |
| *A61K 47/60* | (2017.01) |

(52) U.S. Cl.
CPC ............ *A61K 41/008* (2013.01); *A61K 47/60* (2017.08); *C07F 5/022* (2013.01); *C07F 15/0086* (2013.01)

(58) Field of Classification Search
CPC ............................. C07F 5/022; C07F 15/0086
USPC ............................................. 546/2, 13; 544/1
See application file for complete search history.

(56) References Cited

FOREIGN PATENT DOCUMENTS

| CN | 108299625 A | 7/2018 |
| CN | 113861229 A | 12/2021 |

OTHER PUBLICATIONS

International Search Report of PCT/CN2022/100790, dated Dec. 26, 2022.
Vanitha Ramu et al., Glucose-Appended Platinum(II)-BODIPY Conjugates for Targeted Photodynamic Therapy in Red Light. Chem., Feb. 5, 2018, vol. 57, pp. 1717-1726.
Vanitha Ramu et al., Diplatinum (II), catecholate of photoactive boron -dipyrromethene for lysosome -targeted photo dynamic therapy in red light Inorg. Chem., Jul. 3, 2019, vol. 58, pp. 9067-9075.

*Primary Examiner* — Charanjit Aulakh

(57) ABSTRACT

The present disclosure proposes a BODIPY-based rhombic metal ring, its preparation method, and application in near-infrared region imaging, specifically a BODIPY-based rhombic metal ring M absorbed in the near-infrared first region formed based on a BODIPY-based 120° bipyridyl BODIPY ligand molecule 1 and a 60° methoxy platinum acceptor molecule 2, self-assembled by Pt—N metal coordination bonds. The BODIPY-based rhombic supramolecular metal ring has good solubility and near-infrared fluorescence emission, and it is wrapped by commercial amphiphilic polymer F127 carrier to form F127/M nanoparticles, which successfully have excellent photodynamic and photothermal therapeutic effects in vitro.

9 Claims, 7 Drawing Sheets

BODIPY-BASED RHOMBIC METAL RING, PREPARATION METHOD THEREOF, AND APPLICATION IN NEAR-INFRARED REGION IMAGING

CROSS REFERENCE

The application is a continuation of International Patent Application No. PCT/CN2022/100790 with a filing date of Jun. 23, 2022, designating the United States, now pending, and further claims priority to Chinese Patent Application No. 202210419349.3 with a filing date of Apr. 20, 2022. The content of the aforementioned applications, including any intervening amendments thereto, are incorporated herein by reference.

TECHNICAL FIELD

The present disclosure belongs to the technical field of polymer materials and relates to a BODIPY-based rhombic metal ring, its preparation method, and application in near-infrared region imaging, specifically a BODIPY-based rhombic metal ring M absorbed in the near-infrared first region formed based on a BODIPY-based 120° bipyridyl BODIPY ligand molecule 1 and a 60° methoxy platinum acceptor molecule 2, self-assembled by Pt—N metal coordination bonds.

BACKGROUND

Early 1960s, Pedersen, Lehn, and Cram et al. were the first to discover crown ethers and were pioneers in the study of supramolecular chemistry. Supramolecular chemistry is the science of forming complex, ordered, and functionally specific aggregates through non-covalent bonds, where these non-covalent bonds include hydrogen bond, van der Waals force, π–π stacking, electrostatic interaction, hydrophobic interaction, and metal coordination interaction. Among them, metal coordination interactions are used for the preparation of supramolecular coordination complexes (SCCs), which are two-dimensional (2D) metal rings and three-dimensional (3D) metal cages with well-defined sizes, dimensions and geometries formed by coordination interactions between metals and ligands, due to their strong forces and good orientation. While Treibs and Kreuzer first reported fluoroboron dipyrrole (BODIPY) analogs in 1968, such fluorescent dyes have attracted increasing attention in recent years. As porphyrin analogs, BODIPY has the advantages of large molar extinction coefficient, high quantum yield, tunable photophysical properties, easy modifiability, excellent chemical stability, etc. Therefore, the present disclosure proposes the formation of near-infrared emitting rhombic supramolecular metal macrocycles using 120° BODIPY-based near-infrared emitting bipyridine ligand molecules self-assembled with 60° methoxy platinum acceptors, which mainly: (1) with 60° methoxy platinum acceptors, such that the rhombic supramolecular metal macrocycles of the present disclosure have better solubility than the ligands; (2) the introduction of the BODIPY groups into the bipyridine ligands, increasing the conjugated structure of the supramolecule, such that the rhombic supramolecular metal macrocycles of the present disclosure have excellent near-infrared emission as well as photostability; (3) application in the field of tumor therapy.

SUMMARY OF THE DISCLOSURE

To address the shortcomings of the related art, a first aspect of the present disclosure provides a BODIPY-based 120° bipyridyl BODIPY ligand, having the following chemical structure formula:

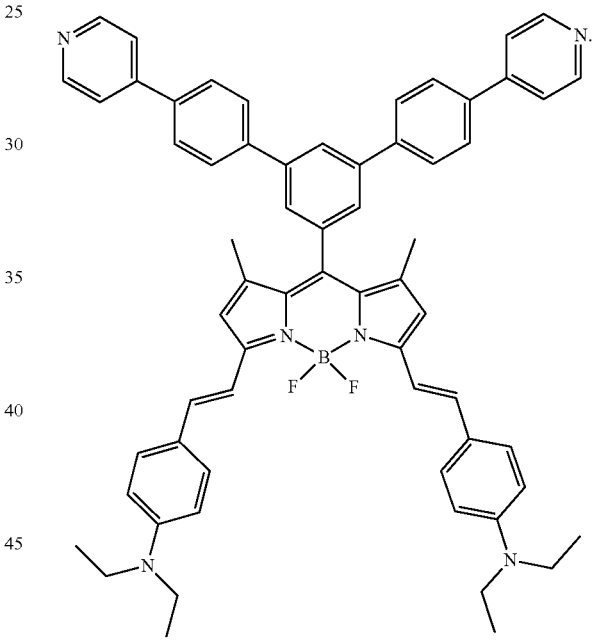

A second aspect of the present disclosure provides a preparation method of a BODIPY-based 120° bipyridyl BODIPY ligand, having the following synthetic route:

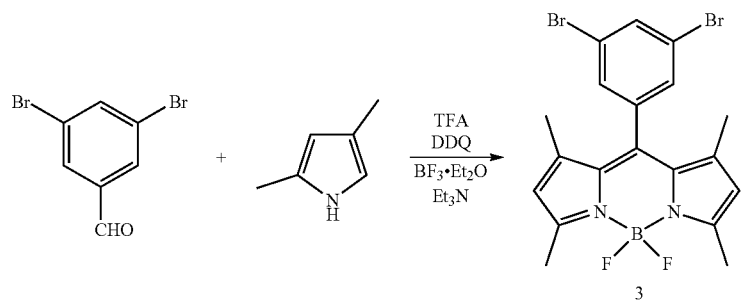

-continued
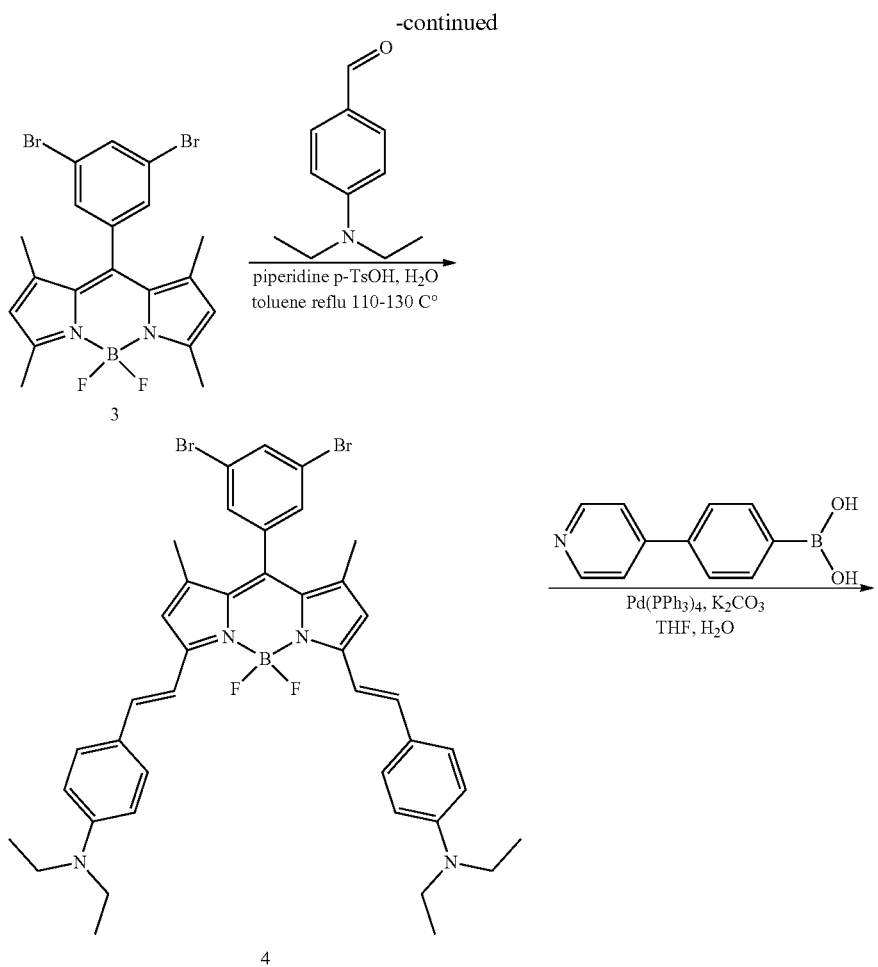
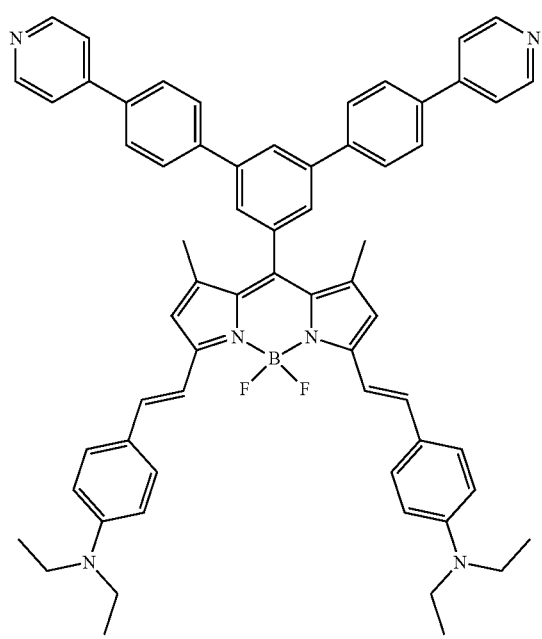

wherein the preparation method comprises:

(1) adding a molecular sieve, a Compound 3, N,N-diethyl-4-aminobenzaldehyde, a p-toluenesulfonic acid monohydrate, and piperidine to a reaction vessel, taking anhydrous toluene as a solvent, heating a reflux reaction at 110-130° C. under nitrogen protection for 48-80 hours, and obtaining a Compound 4 after post-treatment;

in some embodiments, the ratio of the amount of substance of the Compound 3, N,N-diethyl-4-aminobenzaldehyde, p-toluenesulfonic acid monohydrate, and piperidine is 1:2-3:0.04-0.08:0.04-0.08, more preferably 1:2.5:0.05:0.05;

in some embodiments, the reflux reaction is heated is at 120° C. for 72 hours.

(2) adding the Compound 4, pyridine-4-boronic acid, tetrakis(triphenylphosphine)palladium, and potassium carbonate to a reaction vessel, adding a mixture of tetrahydrofuran and water as solvent, and freezing with liquid nitrogen, nitrogen, oil pump, performing a pumping gas treatment; and after three repetitions, carrying out a reaction at 50-70° C. for 10-15 hours under nitrogen protection, and obtaining the BODIPY-based 120° bipyridyl BODIPY ligand 1 after post-treatment;

in some embodiments, the ratio of the amount of substance of the Compound 4, 4-(4-pyridyl)phenylboronic acid, tetrakis(triphenylphosphine)palladium, and potassium carbonate is 1:2-4:0, 1:2-5, more preferably 1:3:0.1:4;

in some embodiments, the reaction is carried out at 65° C. for 12 hours.

In some embodiments, in step (1), the post-treatment is: removing the solvent under reduced pressure with a rotary evaporator, followed by extraction with dichloromethane and water, collecting the organic phase, drying, and filtering with anhydrous magnesium sulfate and then removing the solvent under reduced pressure with a rotary evaporator to obtain a crude product. The Compound 4 is then purified by silica gel column separation using a petroleum ether/dichloromethane mixture of 1:1 by volume as eluent.

In some embodiments, in step (2), the post-treatment is: removing the solvent with a rotary evaporator, extracting with dichloromethane and water, collecting the organic phase, drying and filtering followed by removing the solvent under reduced pressure with a rotary evaporator to obtain a crude product. The BODIPY-based 120° bipyridyl BODIPY ligand molecule 1 is obtained and purified by separation on a silica gel chromatography column using a dichloromethane/methanol mixture of 20:1 volume as eluent.

A third aspect of the present disclosure provides a BODIPY-based rhombic metal ring M, having the following chemical structure formula:

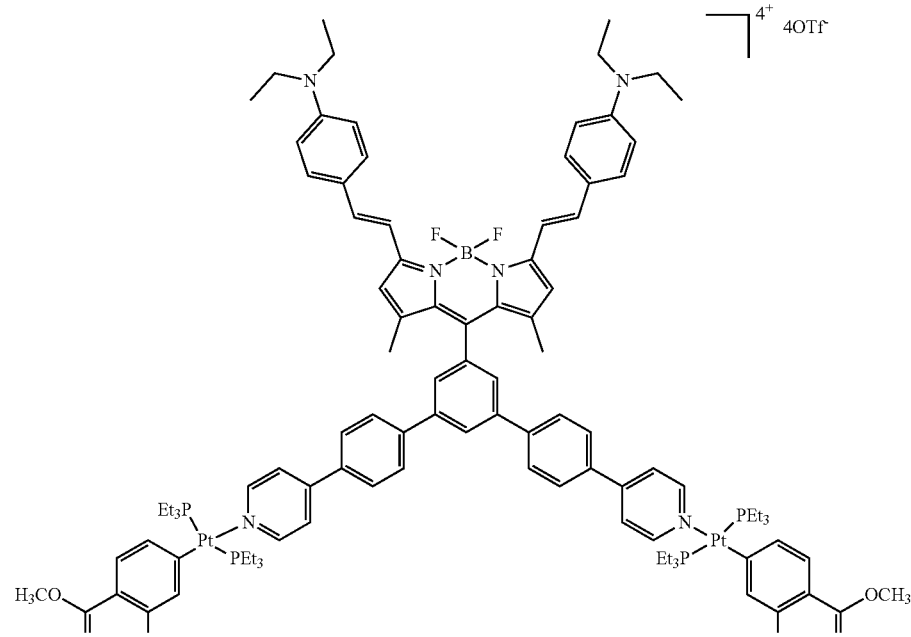

-continued
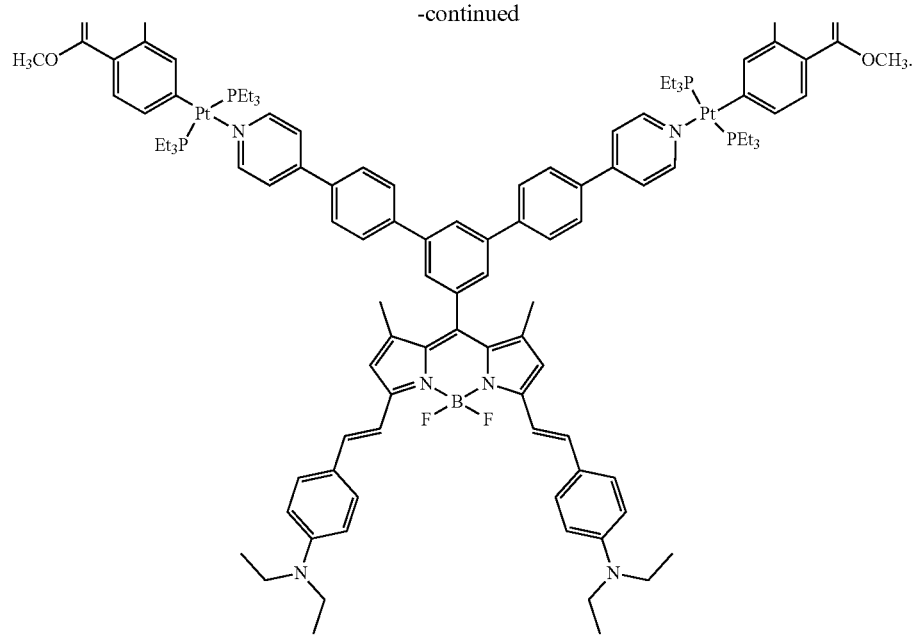
A fourth aspect of the present disclosure provides a preparation method of a BODIPY-based rhombic metal ring, having the following synthetic route:
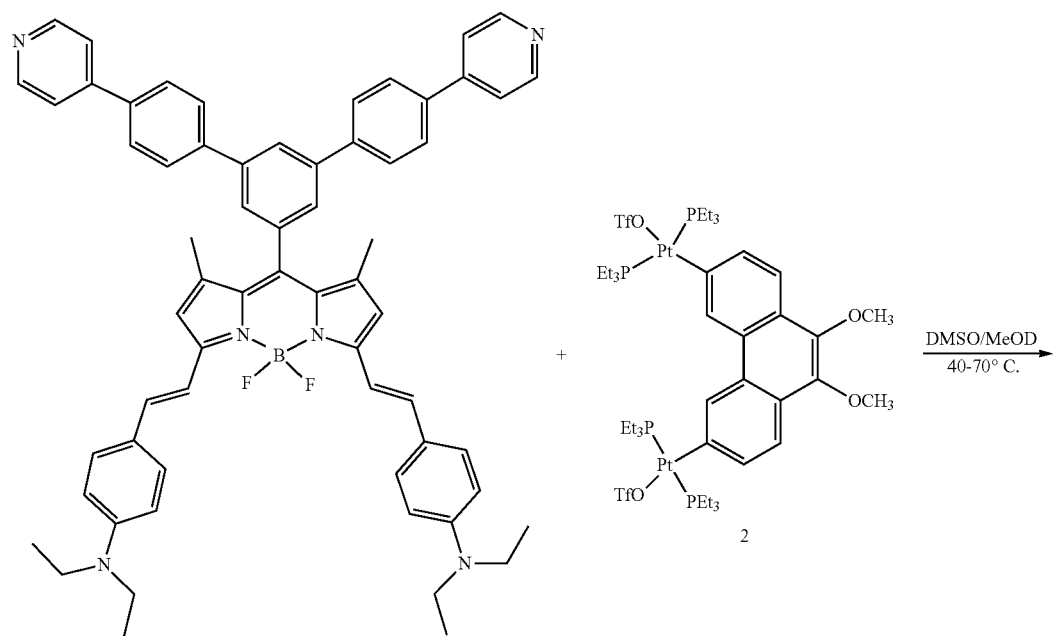

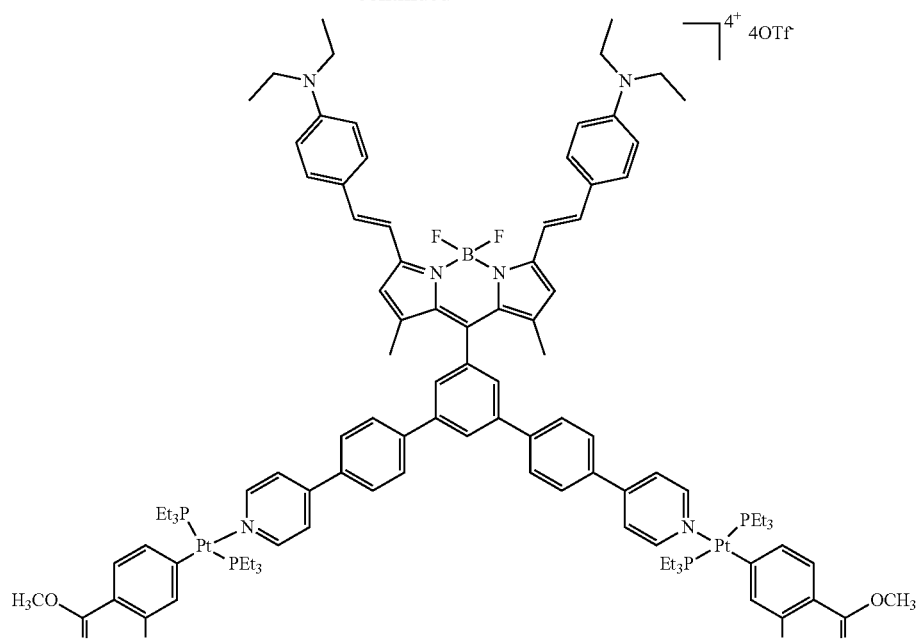
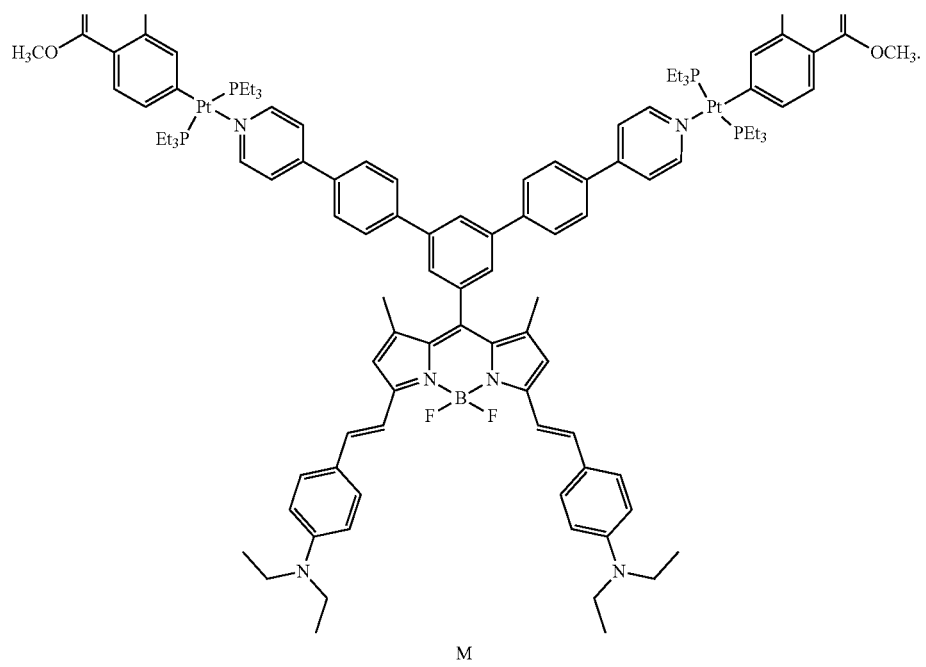
M wherein a BODIPY pyridine ligand 1 and a methoxy platinum acceptor 2 are dissolved in anhydrous methanol with dimethyl sulfoxide and stirred for 8-14 h at 40-70° C. to obtain the BODIPY-based rhombic metal ring M by post-treatment;

in some embodiments, a ratio of the amount of substance of the BODIPY pyridine ligand 1 to the methoxy platinum receptor 2 is 1:0.5-2, more preferably 1:1.

in some embodiments, the stirring is performed for 12 h at 50° C.

in some embodiments, the post-treatment is: filtering and collecting the filtrate, after which using nitrogen flow drumming filtrate to remove the solvent, after which adding 5-10 mL anhydrous ether and shaking to precipitate a black solid, separated by centrifuge and dried to obtain the BODIPY-based rhombic metal ring M;

in some embodiments, a synthetic route of the methoxy platinum acceptor 2 is:

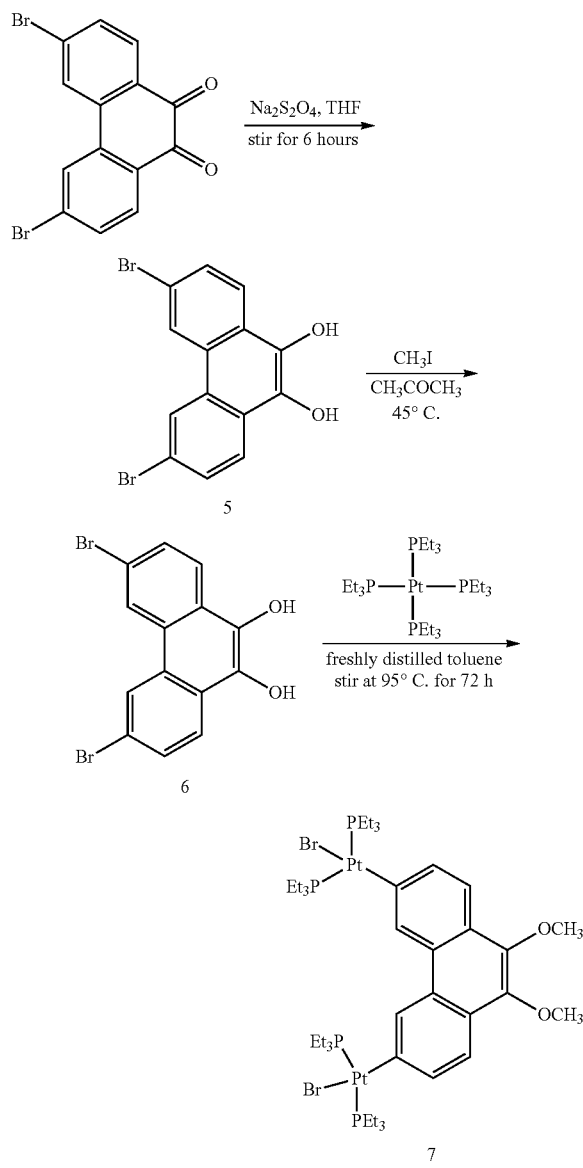

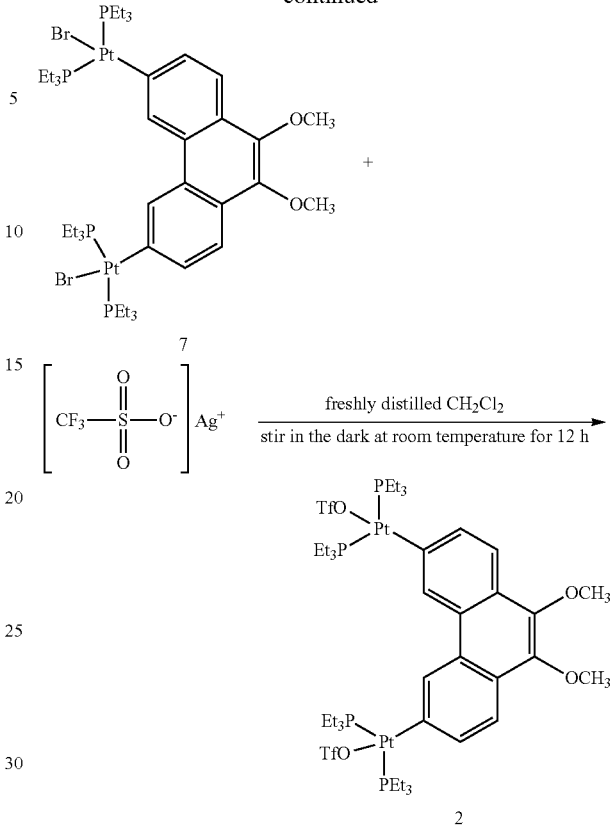

A fifth aspect of the present disclosure provides an application of the BODIPY-based rhombic metal ring for preparation of photothermal agents for tumor NIR photothermal therapy.

A sixth aspect of the present disclosure provides a photothermal agent, prepared by an amphiphilic polymer F127 carrier wrapped with the BODIPY-based rhombic metal ring.

The amphiphilic polymer F127 carrier is Polyoxyethylene-Polyoxypropylene-Polyoxyethylene (PEO.PPO.PEO) triblock copolymer, Planic F127.

The effect of the present disclosure is as follows.

The present disclosure introduces BODIPY-like derivatives into supramolecular coordination complexes to obtain BODIPY-based rhombic metal macrocycles.

The present invention provides a BODIPY-based rhombic metal macrocycle with near-infrared emission as anti-cancer drug applications. The described BODIPY-based rhombic supramolecular metallacycle with good solubility and NIR fluorescence emission is wrapped by a commercial amphiphilic polymer F127 carrier (PEO.PPO.PEO triblock copolymer Planic F127) to form F127/M nanoparticles, which successfully have photodynamic properties and photothermal conversion properties.

DETAILED DESCRIPTION

Figure 1:
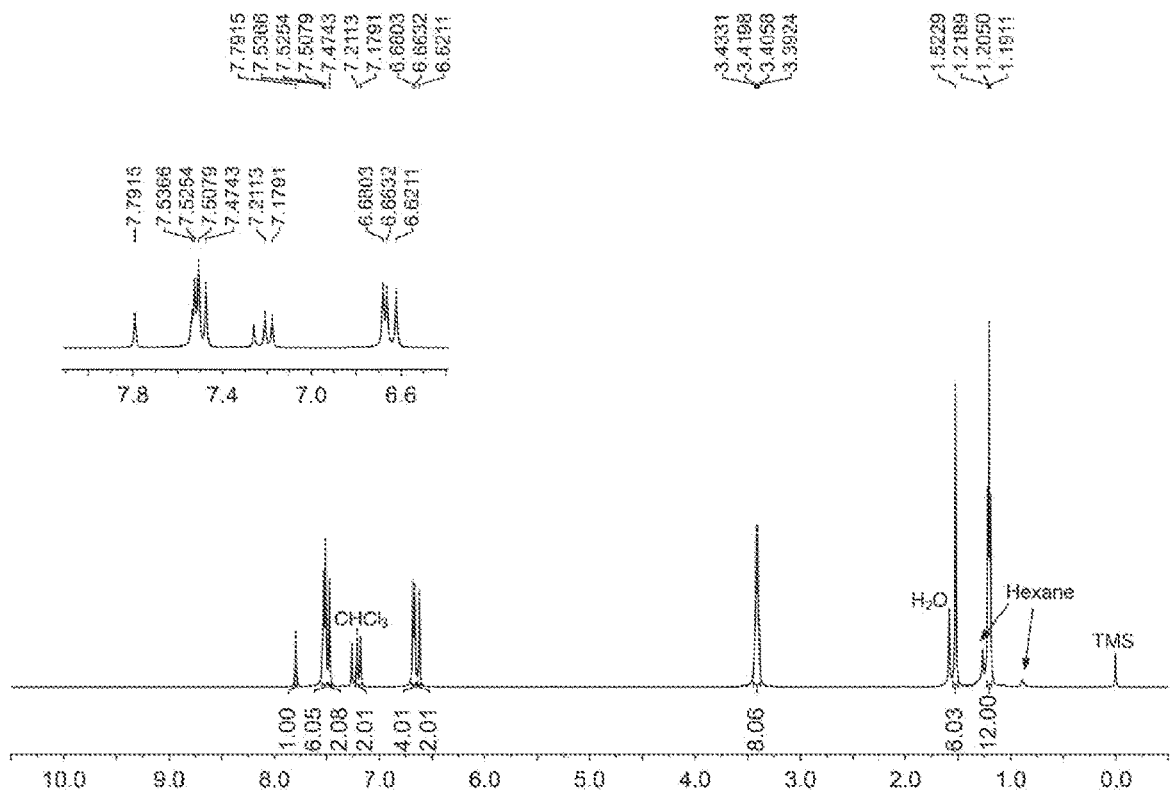
FIG. 1 is an NMR hydrogen spectrum of compound 4 synthesized in Embodiment 1 (deuterated chloroform as solvent).

The present disclosure is further described below in connection with specific embodiments, but the scope of the present disclosure is not limited thereto.

As mentioned, in view of the deficiencies of the related art, the inventors of the present disclosure, after long-term research and extensive practice, have proposed a technical solution of the present disclosure, which is based on at least including: introducing BODIPY-like derivatives into supramolecular coordination complexes to obtain BODIPY-based rhombic metal macrocycles with near-infrared emission. The BODIPY-based rhombic supramolecular metal ring has good solubility and near-infrared fluorescence emission, and it is wrapped by commercial amphiphilic polymer F127 carrier to form F127/M nanoparticles, which successfully have excellent photodynamic therapy and photothermal therapy effect in vitro. In addition, the wrapped metal ring described in the present disclosure, which can be successfully taken up by cells, has powerful killing power against tumor cells.

To make the object, technical solutions, and advantages of the present disclosure more clearly understood, the present disclosure is described in further detail hereinafter in conjunction with the accompanying drawings and embodiments. It can be understood that the specific embodiments described herein are intended to explain the present disclosure only and are not intended to limit the present disclosure. Furthermore, the technical features involved in the various embodiments of the present disclosure described below may be combined with each other as long as they do not constitute a conflict between them.

The present disclosure proposes a BODIPY-based rhombic metal ring M with near-infrared emission; its chemical structure formula is as follows.

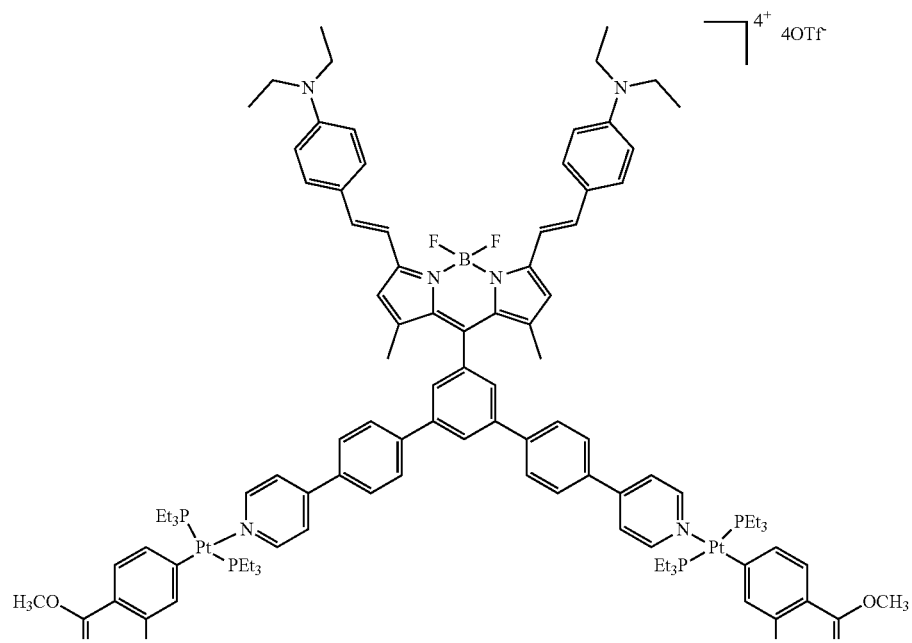

-continued
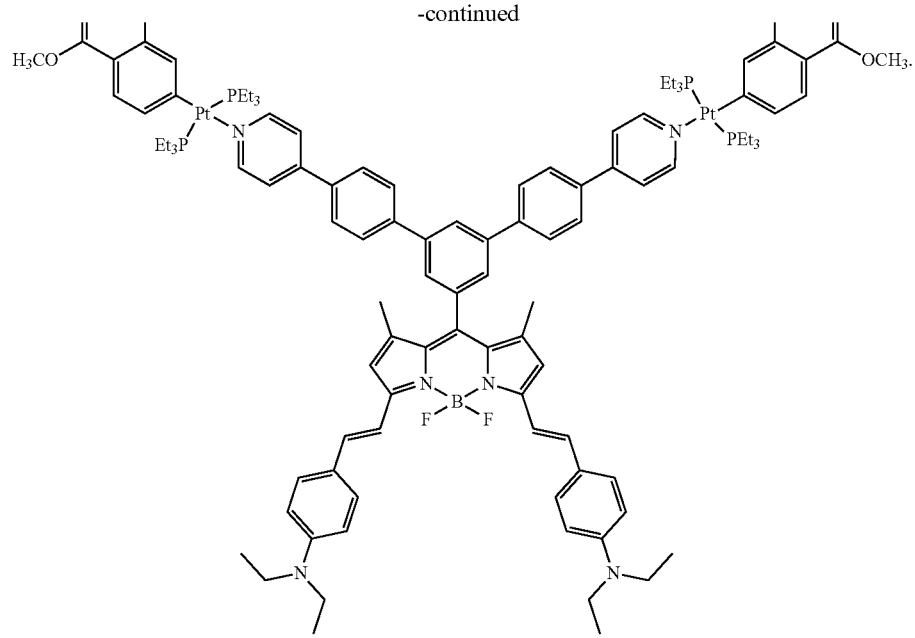
The preparation method of the BODIPY-based rhombic metal ring M with near-infrared emission is based on the following synthetic route.
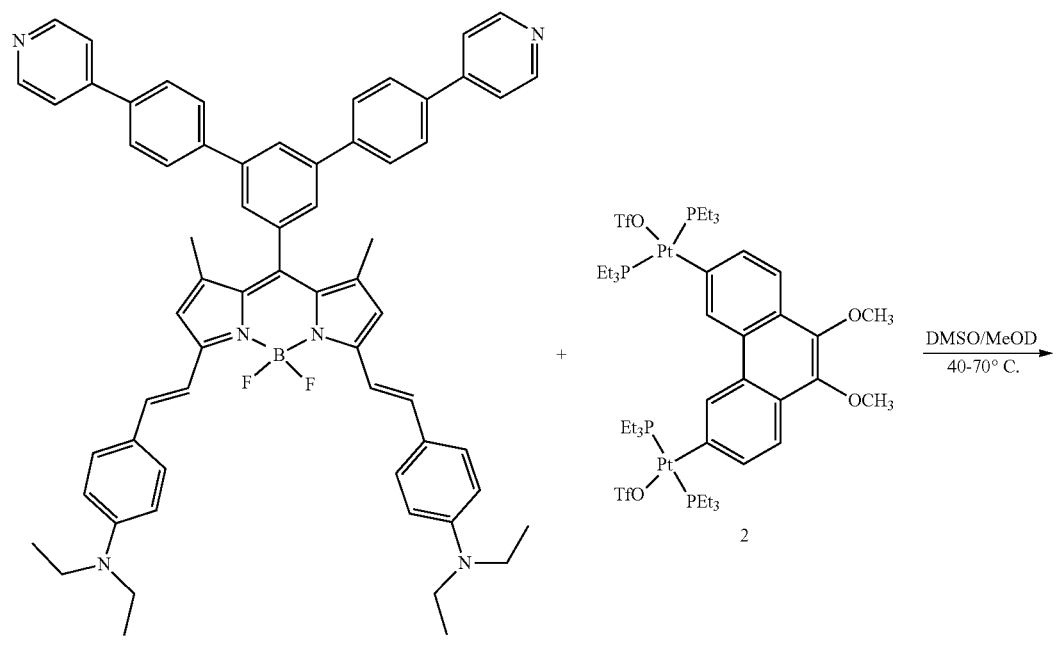

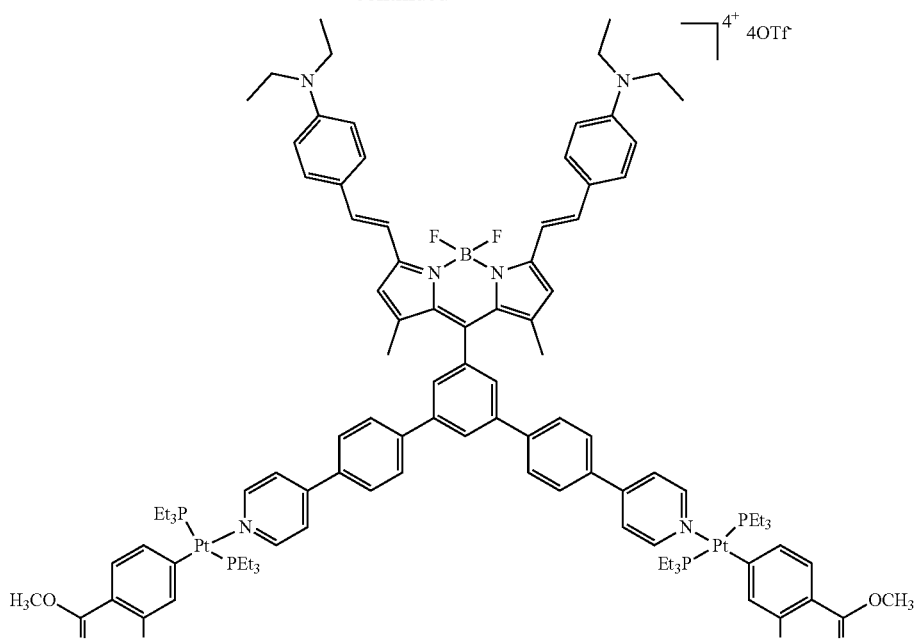
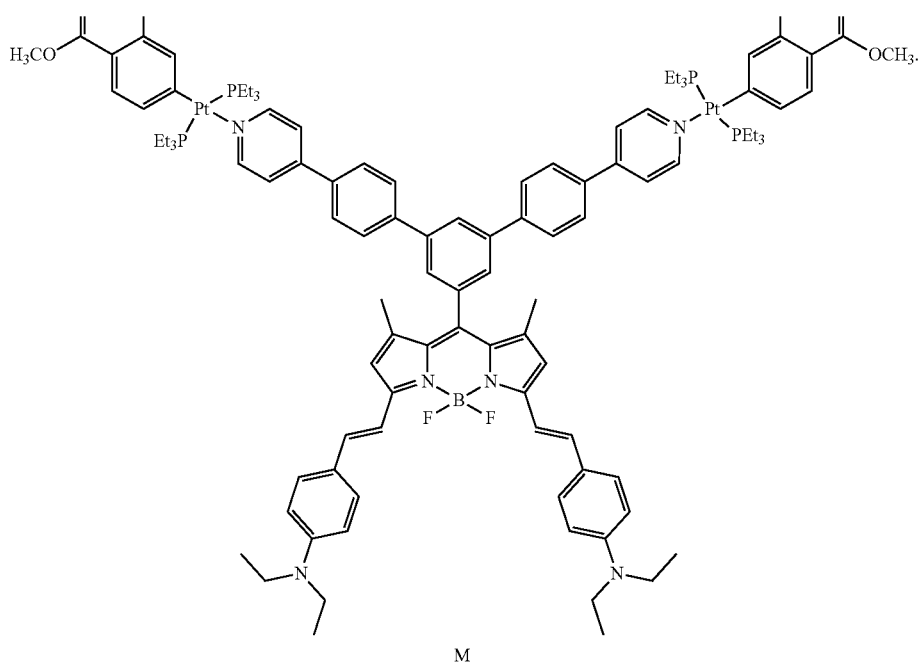
M

The synthesis method is given in detail below.

A BODIPY pyridine ligand 1 and a methoxy platinum acceptor 2 are dissolved in anhydrous methanol with dimethyl sulfoxide and stirred for 8-14 h at 40-70° C. to obtain a BODIPY-based rhombic metal ring M by post-treatment.

In some embodiments, the ratio of the amount of substance of the BODIPY pyridine ligand 1 to the methoxy platinum receptor 2 is 1:0.5-2.

In some embodiments, the method of the post-treatment is that: filtering is performed to collect a filtrate, after which the solvent is removed using nitrogen flow drumming of the filtrate, after which 5-10 mL of anhydrous ether is added and shaken to precipitate a black solid; the black solid is then separated by centrifuge and dried to obtain the BODIPY-based rhombic metal ring M.

The technical solution of the present disclosure is further explained and illustrated below in connection with several embodiments, but the experimental conditions and set parameters therein should not be regarded as limitations of the basic technical solution of the present disclosure. And the scope of the present disclosure is not limited to the following embodiments.

Embodiment 1: 120° BODIPY-Based Bipyridyl Ligand with Near-Infrared Emission

Compound 4: 0.5 mg of molecular sieve is added to a 100 mL round bottom flask, and the reaction flask is operated without water and oxygen, after which Compound 3 (150 mg, 0.3112 mmol), N,N-diethyl-4-aminobenzaldehyde (137.9 mg, 0.7780 mmol), p-toluenesulfonic acid monohydrate (3 mg, 0.01578 mmol), and piperidine (0.15 mL) are added to the flask under nitrogen protection, respectively; anhydrous toluene (9 mL) is added as a reaction solvent, and the reaction is heated at 120° C. under nitrogen protection at reflux for 72 h to obtain a black-green liquid. After the reaction is terminated, the solvent is removed by rotary evaporator under reduced pressure, followed by extraction with dichloromethane and water; the organic phase is collected, dried, and filtered, and then a crude product is obtained by rotary evaporator under reduced pressure. The product is purified by silica gel chromatography column (petroleum ether/dichloromethane, 1/1, v/v) to obtain a black solid (92.0 mg, 37%), decomposition temperature: 134° C.

Figure 2:
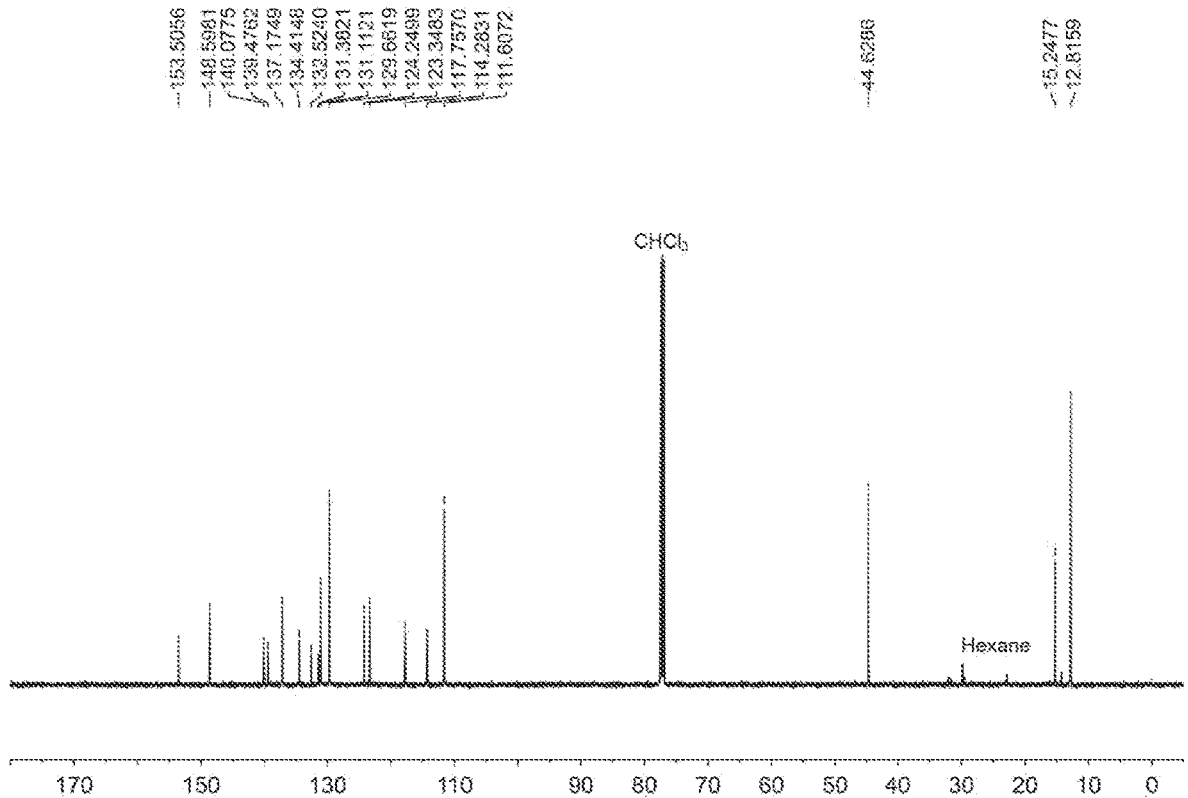
FIG. 2 is an NMR carbon spectrum of compound 4 synthesized in Embodiment I (deuterated chloroform as solvent).
Figure 3A:
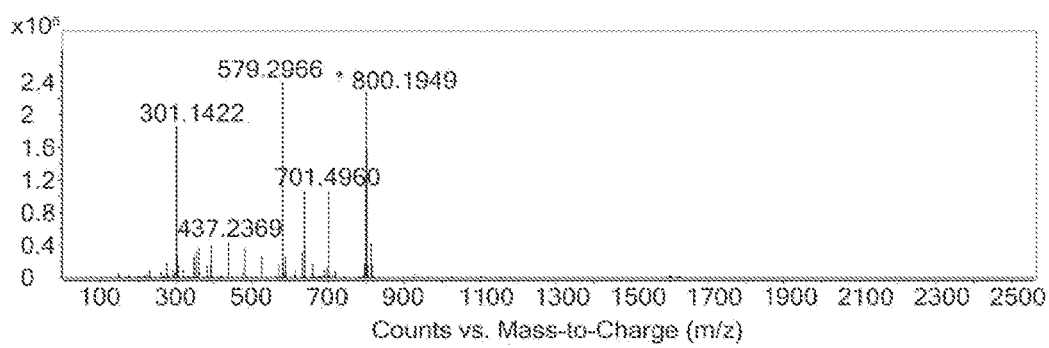
FIG. 3A is a high-resolution mass spectrum of compound 4 synthesized in Embodiment I.
Figure 3B:
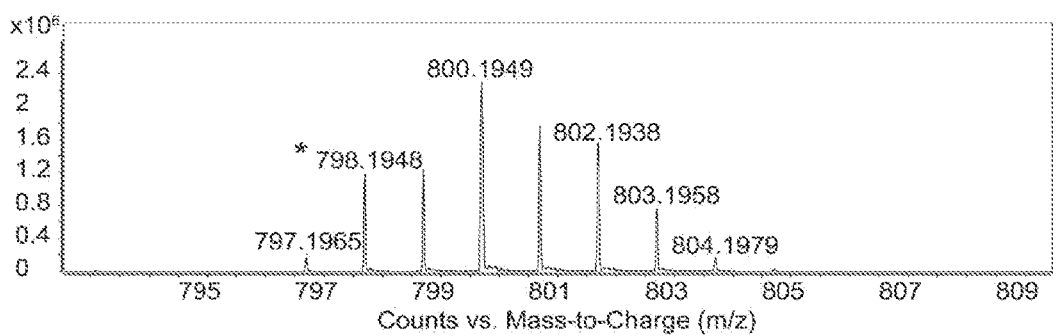
FIG. 3B is a partial enlarged view of FIG. 3A.

Shown in FIGS. 1-3: $^1$H NMR (500 MHz, CDCl$_3$, 298 K) δ (ppm): 7.79 (s, 1H), 7.54-7.49 (m, J=6H), 7.47 (s, 2H), 7.21 (s, 1H), 7.18 (s, 1H), 6.67 (d, J=8.5 Hz, 4H), 6.62 (s, 2H), 3.41 (dd, J=13.7, 6.7 Hz, 8H), 1.52 (s, 6H), 1.21 (t, J=6.9 Hz, 12H). $^{13}$C NMR (126 MHz, CDCl$_3$, 298 K) δ (ppm): 153.51, 148.60, 140.08, 139.48, 137.17, 134.41, 132.52, 131.38, 131.11, 129.66, 124.25, 123.35, 117.76, 114.28, 111.61, 44.63, 15.25, 12.82. ESI-HR-MS: m/z 798.1948 [4+H]$^+$, calcd. for [C$_{41}$H$_{43}$BBr$_2$F$_2$N$_4$H]$^+$, 798.2025.

Preparation of BODIPY-based 120° bipyridyl BODIPY ligand molecule 1.

In a 100 mL Schlenk bottle, 50 mL of a solvent mixture (tetrahydrofuran/water, 4/1, v/v) is added, a long steel needle is placed below the solution and slowly bubbled for 20 min, after which Compound 4 (100.0 mg, 0.1249 mmol), 4-(4-pyridyl)phenylboronic acid (75.59 mg, 0.3748 mmol), potassium carbonate (68.78 mg, 0.4996 mmol), tetrakis(triphenylphosphine)palladium (14.40 mg, 0.01249 mmol) are added to the vial, with evacuation performed three times and heating under nitrogen atmosphere for 12 h at 65° C. After the reaction is terminated, the solvent is removed by rotary evaporator, extracted with dichloromethane and water; the organic phase is collected, dried, and filtered, and then a crude product is obtained by removing the solvent with rotary evaporator under reduced pressure. The product is purified by silica gel chromatography column (dichloromethane/methanol, 20/1, v/v) to obtain a black solid (100.0 mg, 85%), decomposition temperature: 201° C.

Figure 4:
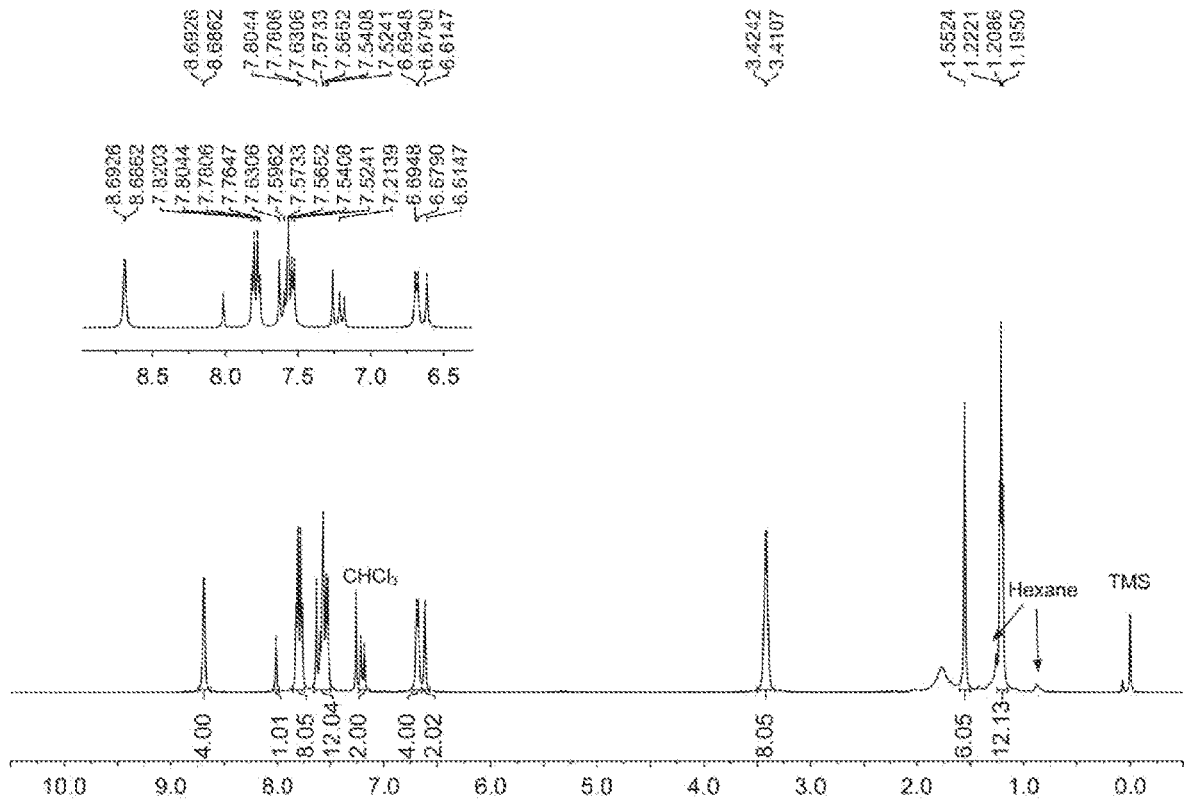
FIG. 4 is an NMR hydrogen spectrum of ligand 1 synthesized in Embodiment I (deuterated chloroform as solvent).
Figure 5:
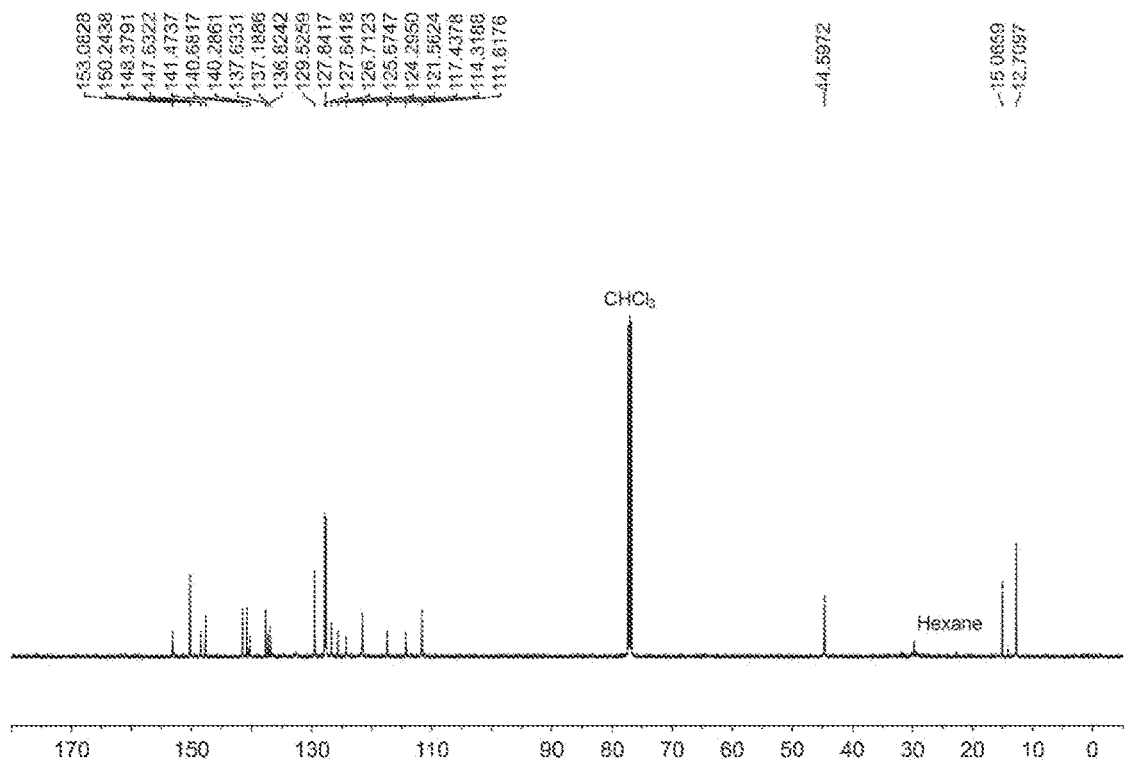
FIG. 5 is an NMR carbon spectrum of ligand 1 synthesized in Embodiment I (deuterated chloroform as solvent).
Figure 6A:
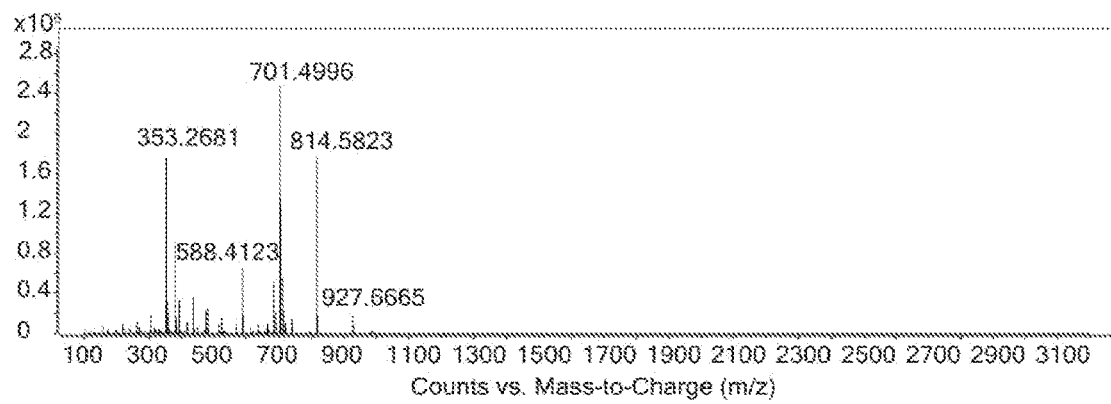
FIG. 6A is a high-resolution mass spectrum of ligand 1 synthesized in Embodiment I.
Figure 6B:
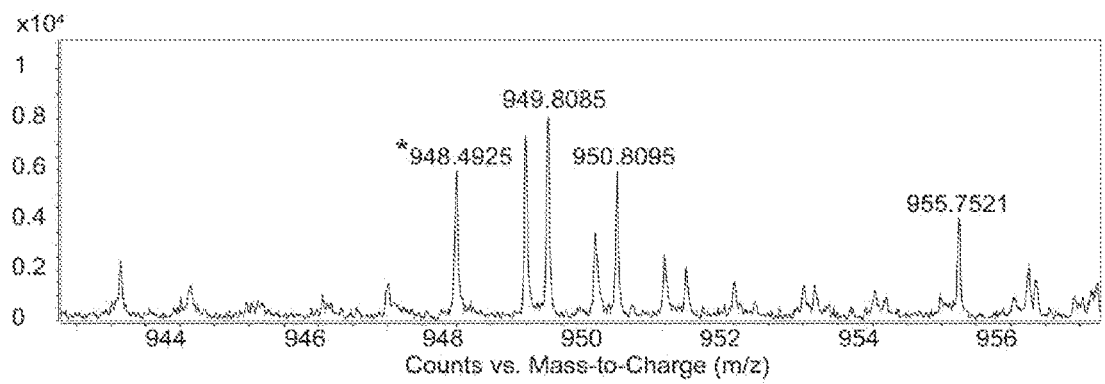
FIG. 6B is a partial enlarged view of FIG. 6A.

Shown in FIGS. 4-6: $^1$H NMR (500 MHz, CDCl$_3$, 298 K) δ (ppm): 8.69 (d, J=3.2 Hz, 4H), 8.02 (s, 1H), 7.79 (dd, J=19.8, 8.0 Hz, 8H), 7.66 -7.50 (m, 12H), 7.20 (d, J=16.0 Hz, 2H), 6.69 (d, J=7.9 Hz, 4H), 6.61 (s, 2H), 3.42 (d, J=6.7 Hz, 8H), 1.55 (s, 6H), 1.21 (t, J=6.8 Hz, 12H). $^{13}$C NMR (126 MHz, CDCl3, 298 K) δ (ppm): 153.15, 150.31, 148.44, 147.70, 141.54, 140.74, 140.35, 137.70, 137.25, 136.89, 129.59, 127.90, 127.70, 126.78, 125.74, 124.36, 121.63, 117.50, 114.38, 110.68, 44.66, 15.13, 12.77. ESI-HR-MS: in/z 948.4925 [1+H]$^+$, calcd. for [C$_{63}$H$_{59}$BF$_2$N$_6$H]$^+$, 948.4971.

Embodiment 2: 60° Methoxy Platinum Receptor

60° methoxy platinum receptor molecule 2: synthesized according to the literature. Compound 7 (30.0 mg, 0.0239 mmol), silver trifluoromethanesulfonate (36.8 mg, 0.143 mmol) is added to an 8 mL sample vial and acetone (7 mL) is added to dissolve. The reaction undergoes under stirring for 12 h at room temperature and protected from light. After the reaction is terminated, filtering is performed and the solvent is compressed with a nitrogen stream to obtain a reddish brown solid (25.2 mg, 76%).

Figure 7:
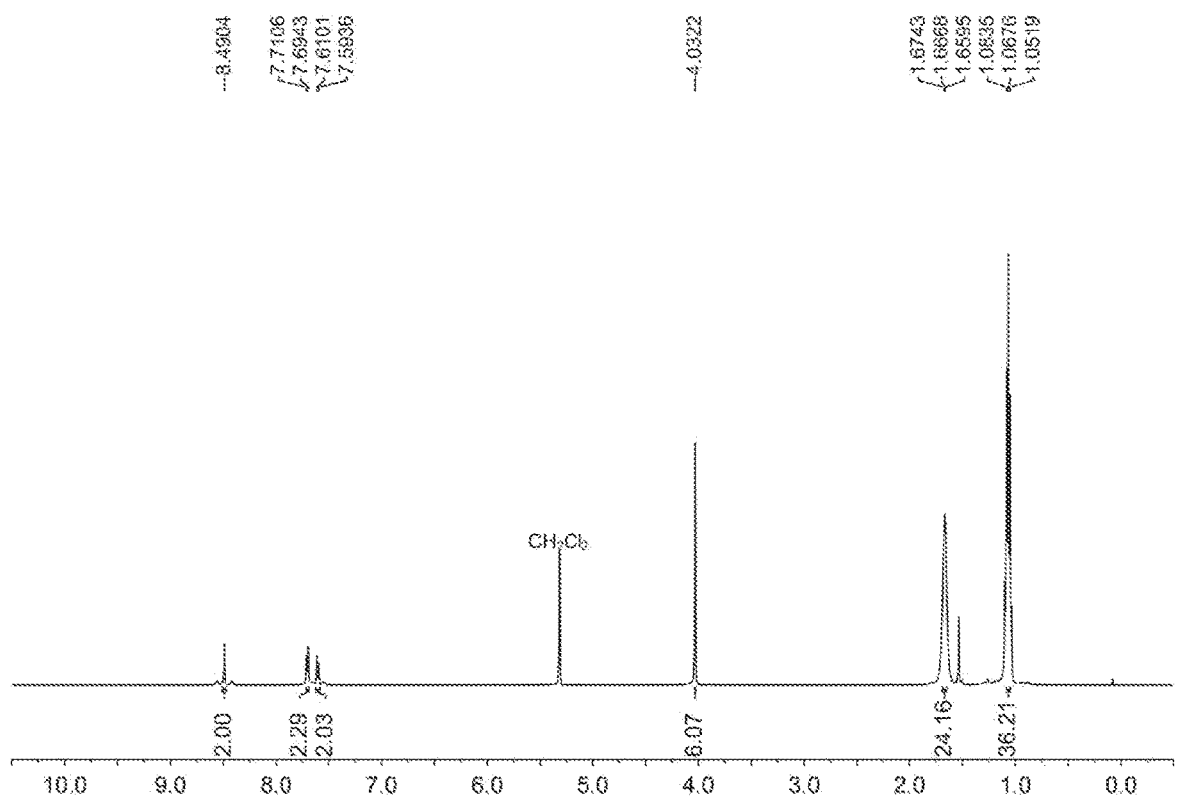
FIG. 7 is an NMR hydrogen spectrum of receptor 2 synthesized in Embodiment II (deuterated dichlor as solvent).
Figure 8:
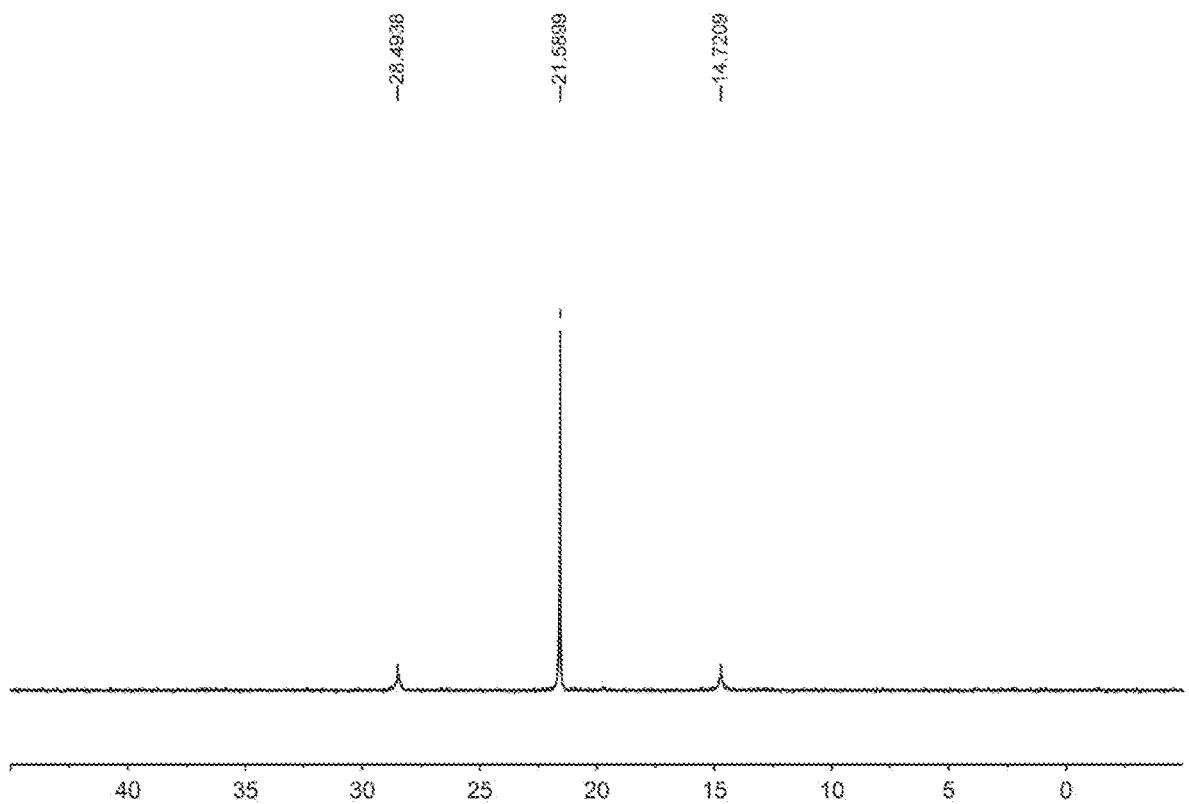
FIG. 8 is an NMR hydrogen spectrum of receptor 2 synthesized in Embodiment II (deuterated methanol as solvent).

Shown in FIGS. 7-8: $^1$H NMR (500 MHz, CD$_2$Cl$_2$, 298 K) δ (ppm): 8.49 (s, 2H), 7.70 (d, J=8.2 Hz, 2H), 7.60 (d, J=8.3 Hz, 2H), 4.03 (s, 6H), 1.69-1.65 (m, 24H), 1.08 -1.05 (m, 36H). $^{31}$P {$^1$H} NMR (202 MHz, MeOD-d$_4$, 298 K) δ (ppm): 21.59 ppm (s, $^{195}$Pt satellites, $^1$J$_{Pt-P}$=2782.5 Hz).

Embodiment 3: BODIPY-Based Rhombic Metal Ring M with Near-Infrared Emission

Preparation of BODIPY-based rhombic metal ring M.

Compound 1 (6.800 mg, 7.165 μmol) and Compound 2 (10.00 mg, 7.165 μmol) are dissolved in 1.0 mL of a solvent mixture (dimethyl sulfoxide/methanol, 1/1, v/v) and heated at 50° C. for 12 h. After the reaction is terminated, t filtering is performed and the solvent is compressed with a nitrogen stream, and a solid is precipitated by adding anhydrous ether (7 mL) and mixed well, and then centrifuged and dried to obtain a black solid (15.5 mg, 92%).

Figure 9:
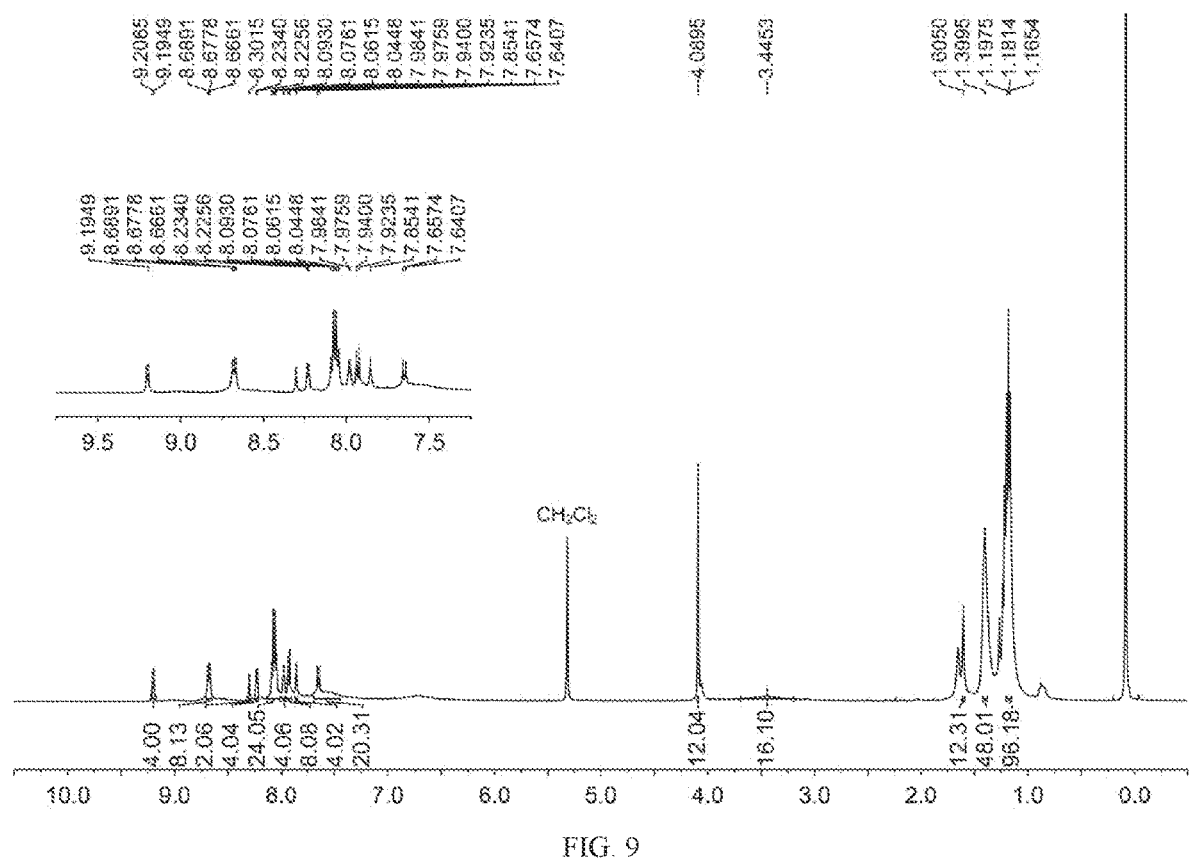
FIG. 9 is an NMR hydrogen spectrum of metal ring M synthesized in Embodiment III (deuterated dichlor as solvent).
Figure 10:
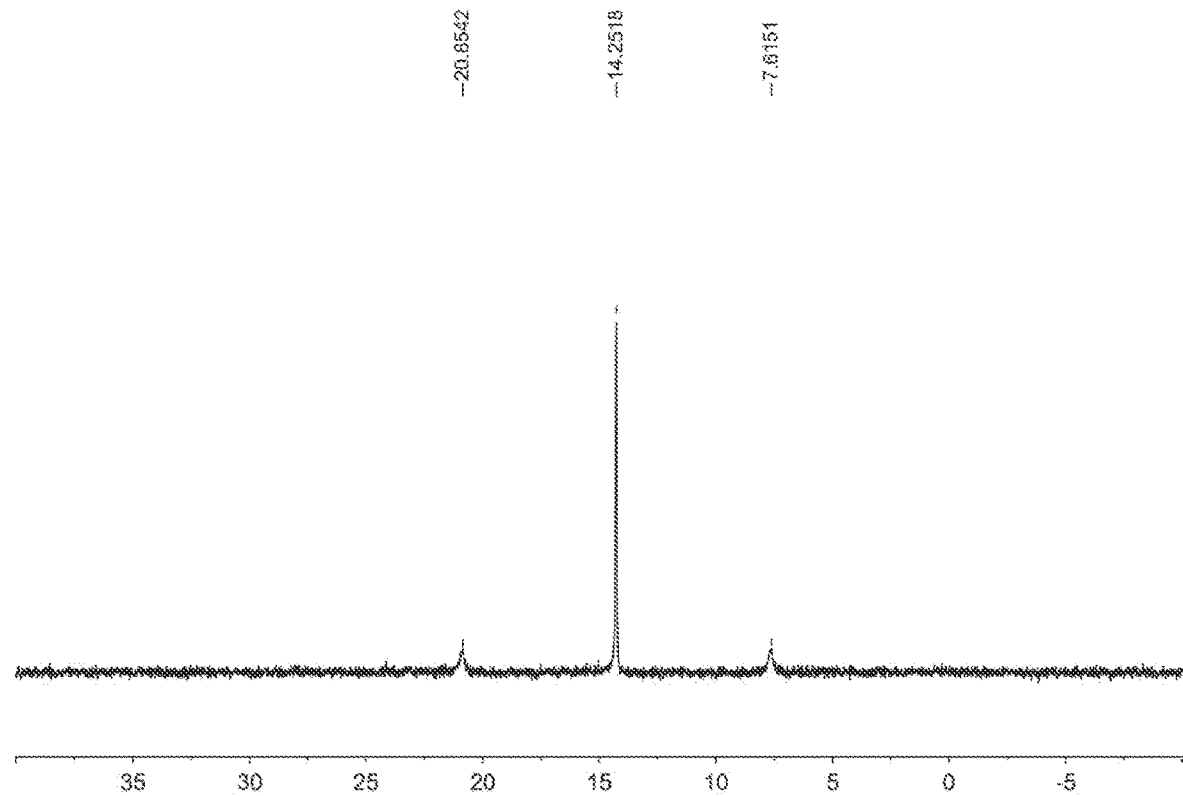
FIG. 10 is an NMR phosphorus spectrum of metal ring M synthesized in Embodiment III (deuterated methanol as solvent).
Figure 11:
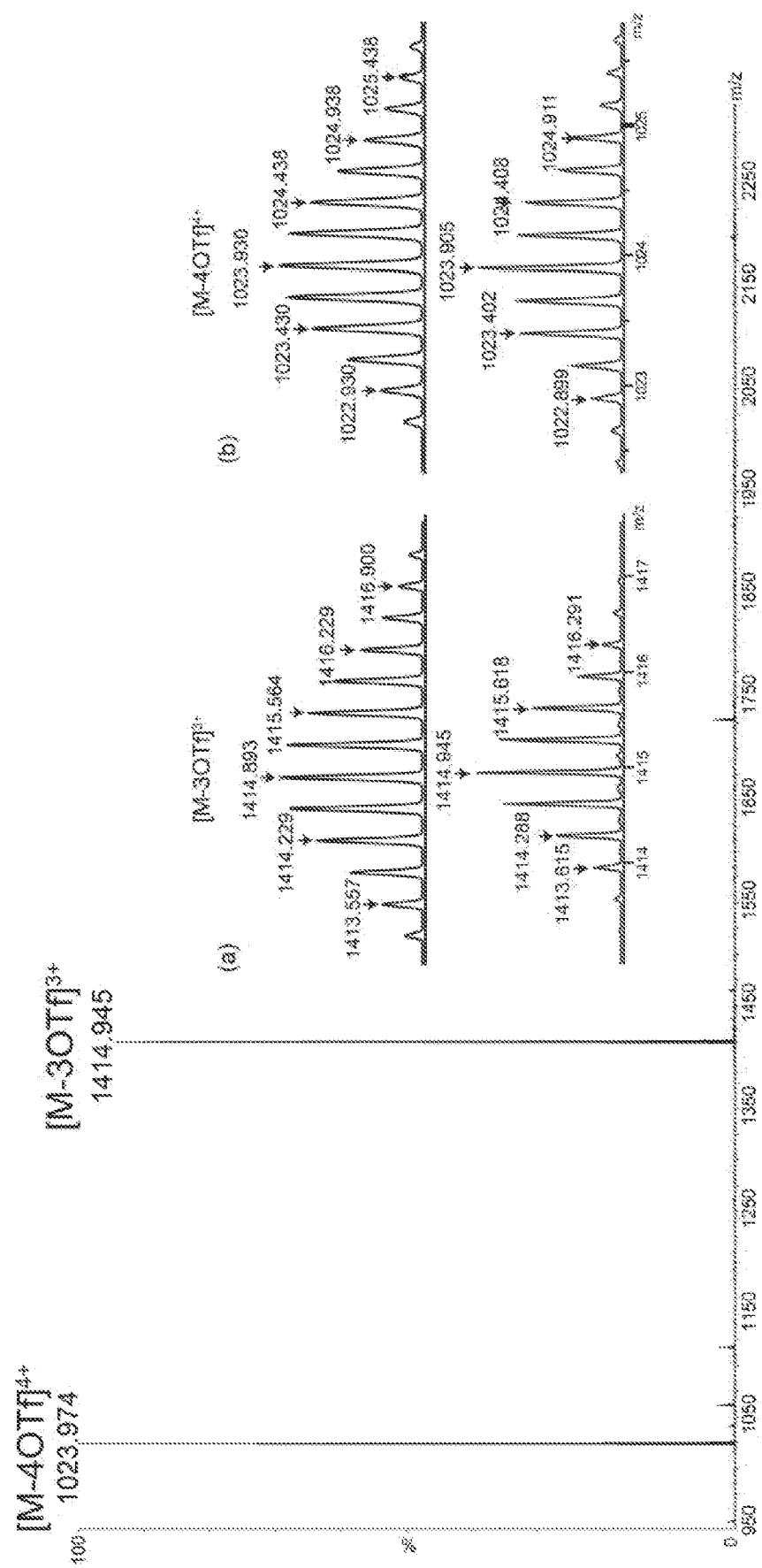
FIG. 11 is an electrospray flight mass spectrum of metal ring M synthesized in Embodiment III.

Shown in FIGS. 9-11: $^1$H NMR (500 MHz, CD$_2$Cl$_2$, 298 K) δ (ppm): 9.20 (d, J=5.8 Hz, 4H), 8.70-8.65 (m, 8H), 8.30 (s, 2H), 8.23 (d, J=4.2 Hz, 4H), 8.07 (dd, J=15.7, 8.07 (dd, J=15.7, 8.4 Hz, 24H), 7.98 (d, J=4.1 Hz, 4H), 7.93 (d, J=8.2 Hz, 8H), 7.85 (s, 4H), 7.65 (d, J=8.3 Hz, 20H), 4.09 (s, 12H), 3.45 (s, 16H), 1.60 (s, 12H), 1.40 (s, 48H), 1.20-1.15 (m, 96H). $^{31}$P {$^1$H} NMR (202 MHz, MeOD-d$_4$, 298 K) δ (ppm): 14.25 ppm (s, $^{195}$Pt satellites, $^1$J$_{Pt-P}$=2674.3 Hz). ESI-TOF-MS: in/z 1023.905 [M−40Tf]4$^+$, 1414.945 [M−30Tf]$^{3+}$.

Embodiment 4: In Vitro Photothermal Effect of F127/M Nanoparticles

F127/M nanoparticles are prepared by precipitation method. First, F127 (10 mg) is weighed and dissolved in deionized water (10 mL) and stirred at room temperature for 30 min, followed by weighing the rhombic metal ring M (2 mg) and dissolving it in acetone (1 mL); the mixture is added slowly dropwise to the aqueous F127 solution stirred at room temperature and stirring openly overnight to evaporate the acetone. The next day it is filtered through an aqueous filter head (0.45 μm) to obtain a translucent dark brown liquid, after which it is lyophilized using a freeze dryer to obtain a dark brown solid.

1.0 mL of aqueous F127/M nanoparticle solution (20 μM) is continuously irradiated by a 660 nm laser at different power densities (0.3, 0.7, 1.0, 1.5, 1.8 W/cm²), the aqueous F127/M nanoparticle solution with different conditions is irradiated for 600 s, and the temperature changes at different powers are recorded with an infrared imager at 60 s intervals.

1.0 mL of aqueous F127/M nanoparticle solution (20 μM) is continuously irradiated with a 660 nm, 1.8 W/cm² laser over 10 min and then naturally cooled to room temperature over 20 min. Water is used as a control group.

Figure 12:
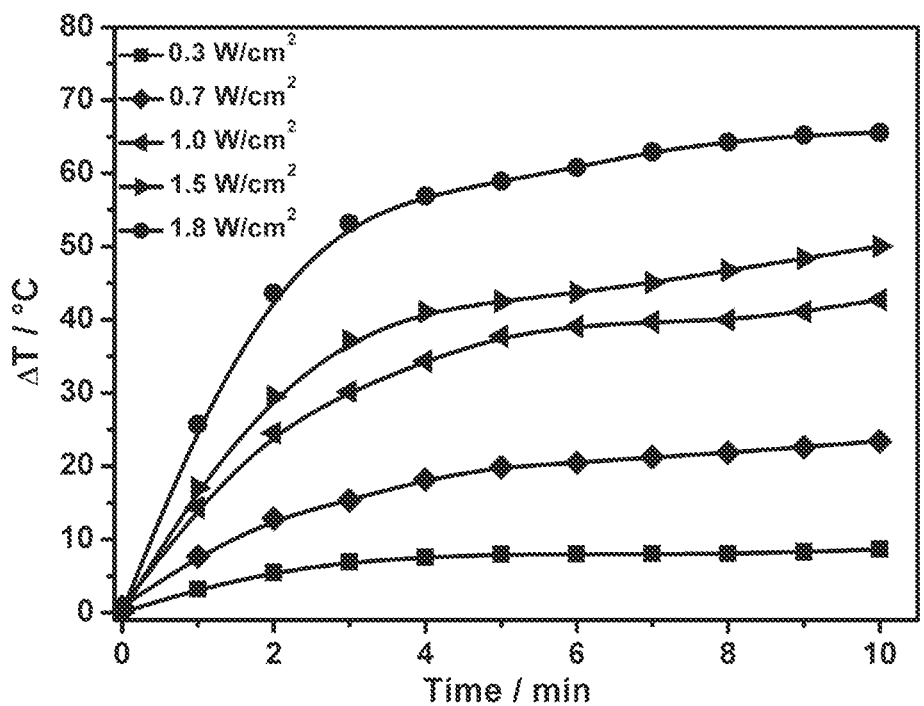
FIG. 12 is an in vitro power-dependent photothermal effect in Embodiment IV.

As shown in FIG. 12, the temperature of the aqueous F127/M nanoparticle solution increases significantly with increasing laser power density (from 0.3 to 1.8 W/cm²), showing a power dependence, and the temperature increase of the aqueous F127/M nanoparticle solution of 20 μM reaches 63.9° C., much higher than that of water at 8.4° C.

Figure 13:
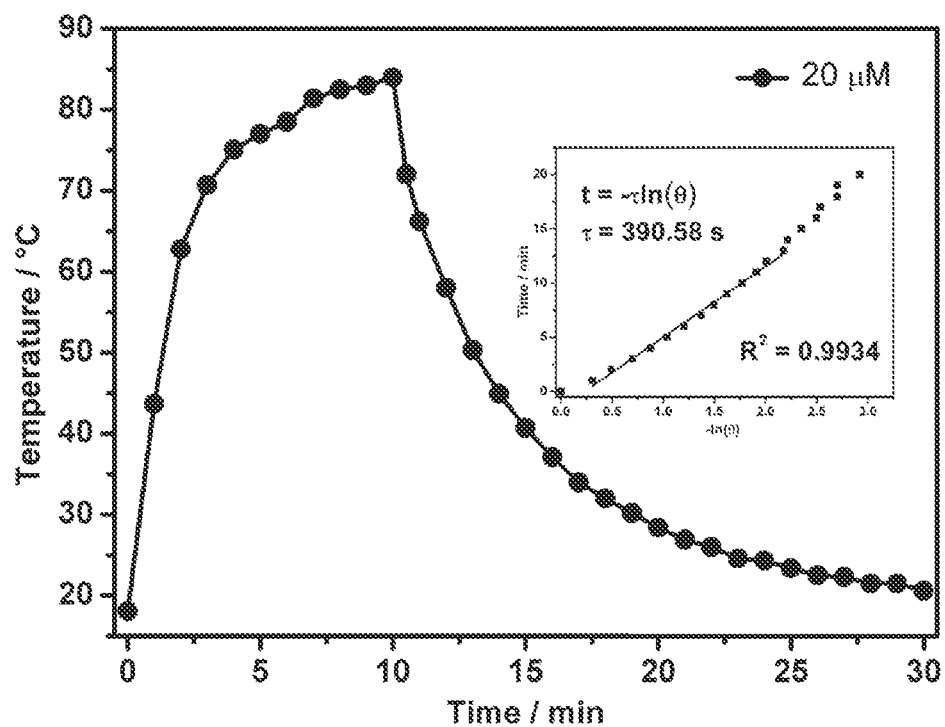
FIG. 13 is an in vitro photothermal effect in Embodiment IV.

As shown in FIG. 13, the temperature of the aqueous solution of F127/M nanoparticles (20 μM) reaches 84° C., while the temperature of pure water changes very little. This large temperature increase proves the strong photothermal conversion ability of F127/M nanoparticles, and the photothermal conversion efficiency is calculated to be 36%.

What is claimed is:

1. A BODIPY-based 120° bipyridyl BODIPY ligand, having the following chemical structure formula:

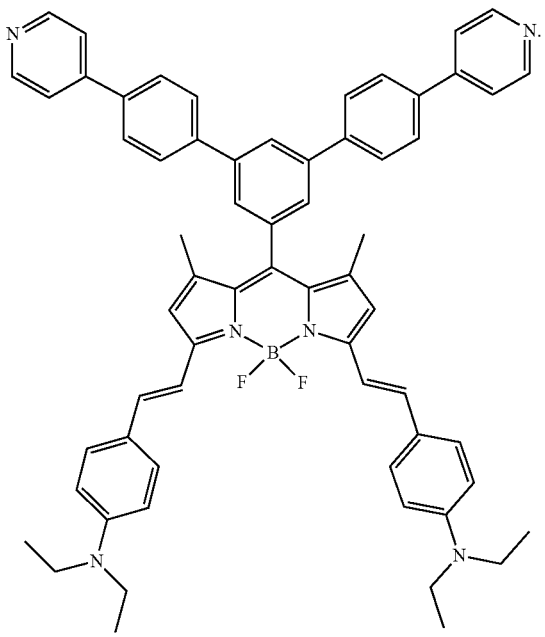

2. A preparation method of a BODIPY-based 120° bipyridyl BODIPY ligand, having the following synthetic route:

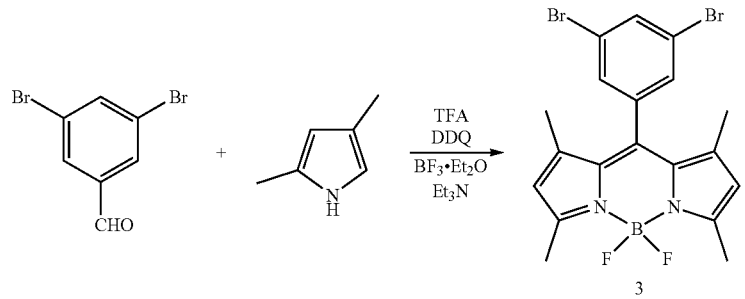

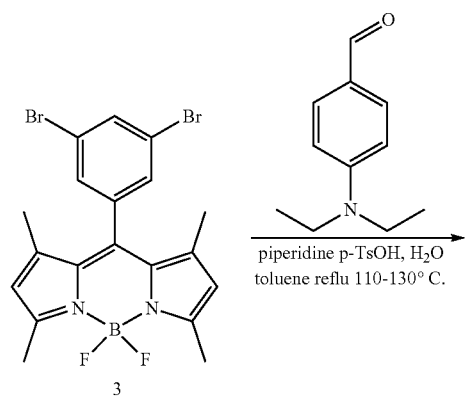

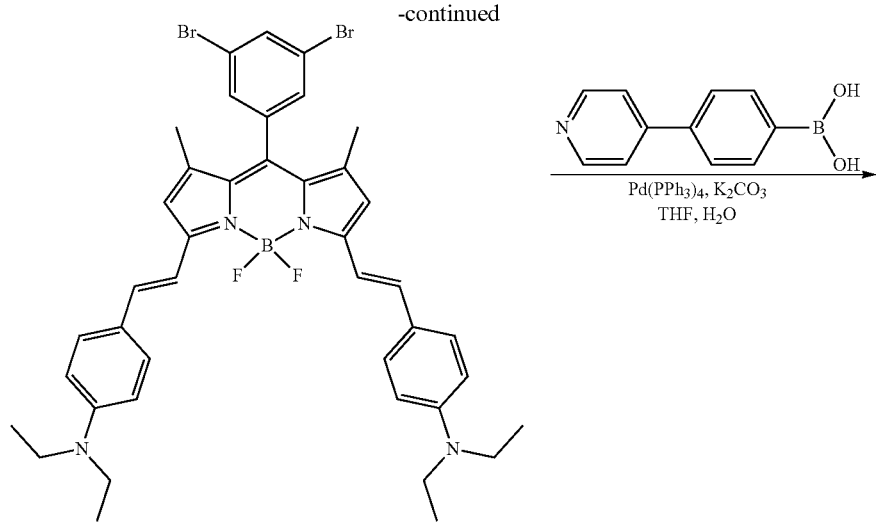

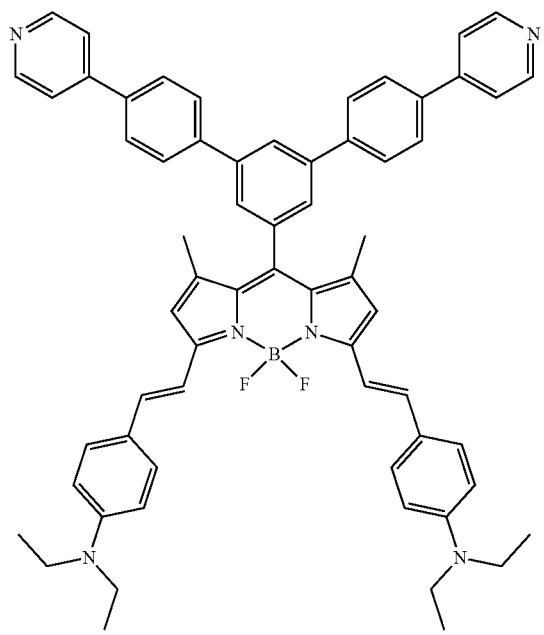

wherein the preparation method comprises:
(1) adding a molecular sieve, a Compound 3, N,N-diethyl-4-aminobenzaldehyde, a p-toluenesulfonic acid monohydrate, and piperidine to a reaction vessel, taking anhydrous toluene as a solvent, heating a reflux reaction at 110-130° C. under nitrogen protection for 48-80 hours, and obtaining a Compound 4 after post-treatment,
(2) adding the Compound 4, pyridine-4-boronic acid, tetrakis(triphenylphosphine)palladium, and potassium carbonate to a reaction vessel, adding a mixture of tetrahydrofuran and water as solvent, and freezing with liquid nitrogen, nitrogen, oil pump, performing a pumping gas treatment; and after three repetitions, carrying out a reaction at 50-70° C. for 10-15 hours under nitrogen protection, and obtaining the BODIPY-based 120° bipyridyl BODIPY ligand 1 after post-treatment.

3. A BODIPY-based rhombic metal ring, having the following chemical structure formula:
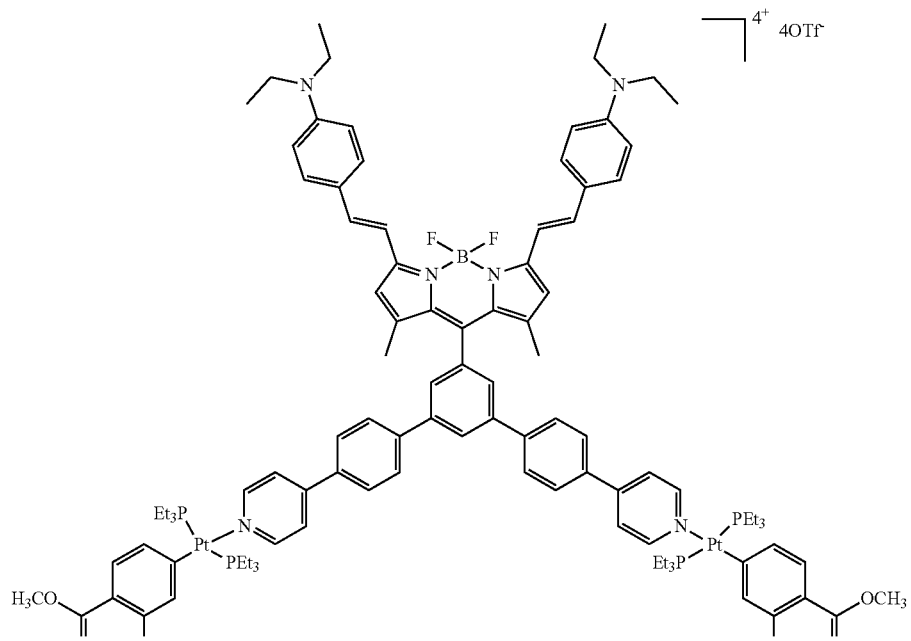
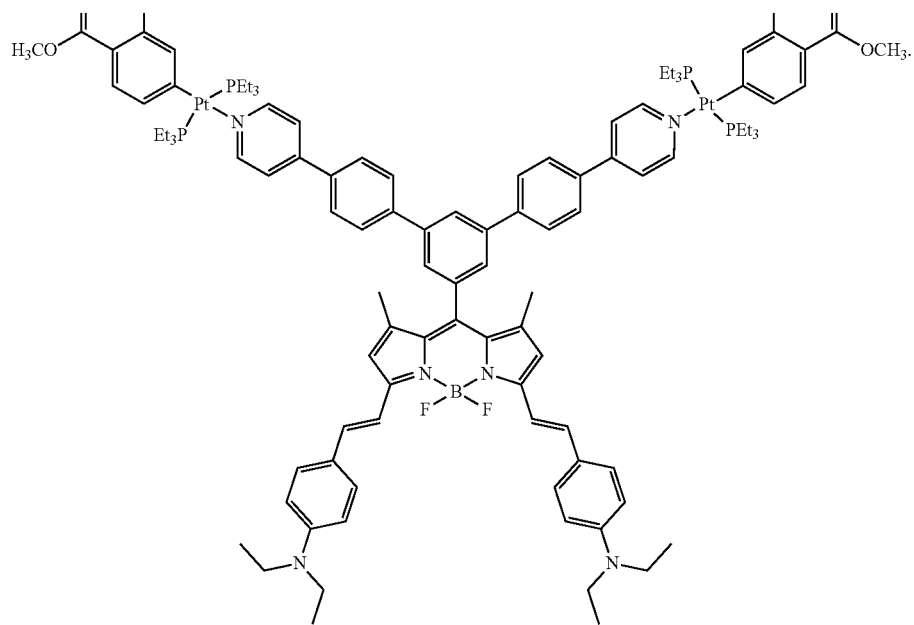

4. A preparation method of a BODIPY-based rhombic metal ring, having the following synthetic route:
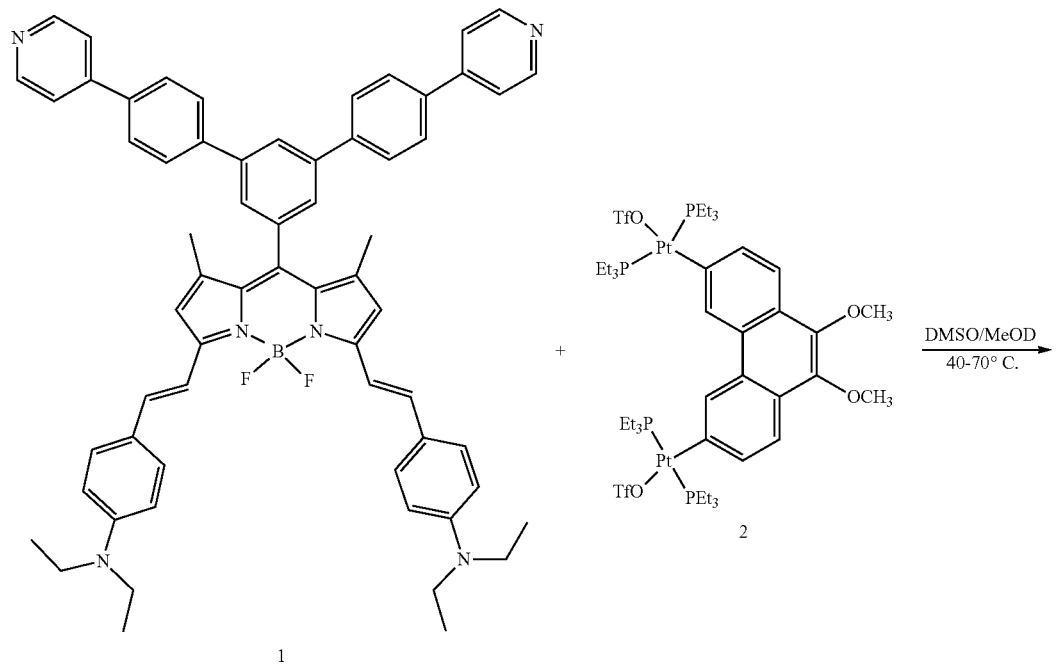
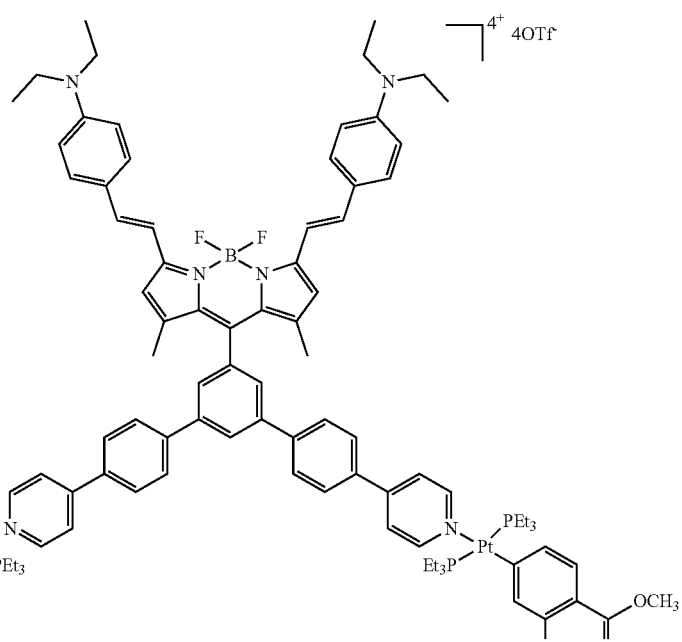

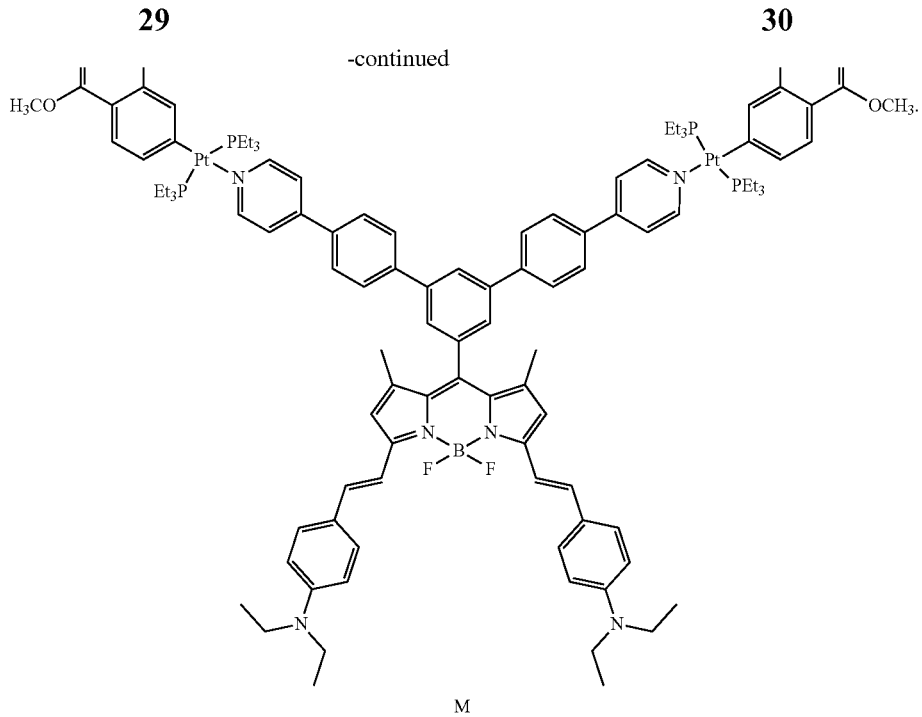

M wherein a BODIPY pyridine ligand 1 and a methoxy platinum acceptor 2 are dissolved in anhydrous methanol with dimethyl sulfoxide and stirred for 8-14 h at 40-70° C. to obtain the BODIPY-based rhombic metal ring M by post-treatment.

5. The method according to claim 4, wherein a ratio of the amount of substance of the BODIPY pyridine ligand 1 to the methoxy platinum receptor 2 is 1:0.5-2.

6. The method according to claim 5, wherein the ratio of the amount of substance of the BODIPY pyridine ligand 1 to the methoxy platinum receptor 2 is 1:1.

7. The method according to claim 4, wherein the stirring is performed for 12 h at 50° C.

8. The method according to claim 4, wherein a synthetic route of the methoxy platinum acceptor 2 is:

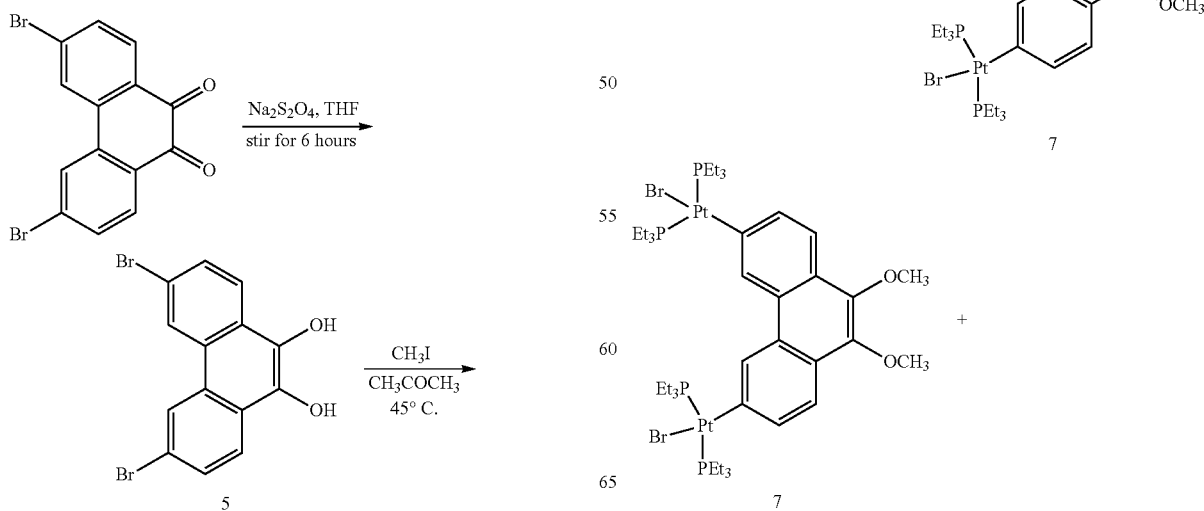

-continued
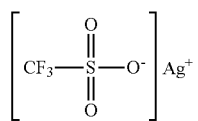 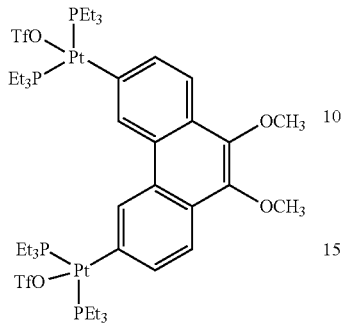
9. A photothermal agent, prepared by an amphiphilic polymer F127 carrier wrapped with the BODIPY-based rhombic metal ring according to claim 3.
* * * * *